United States Patent [19]

Slingluff

[11] 4,105,732

[45] Aug. 8, 1978

[54] RADIOGRAPHIC OPAQUE AND CONDUCTIVE STRIPED MEDICAL TUBES

[75] Inventor: Eugene L. Slingluff, East Troy, Wis.

[73] Assignee: Krandex Corp., Milwaukee, Wis.

[21] Appl. No.: 772,192

[22] Filed: Feb. 25, 1977

Related U.S. Application Data

[62] Division of Ser. No. 634,075, Nov. 21, 1975, Pat. No. 4,027,659.

[51] Int. Cl.² ............................................ A61M 25/00
[52] U.S. Cl. .................................... 264/104; 128/2 M; 128/348; 138/118; 252/502; 252/506; 252/518; 264/105; 264/173; 264/177 R
[58] Field of Search ........... 264/104, 105, 173, 177 R; 252/502, 478, 518, 506; 218/2 M, 349 R, 348; 138/118

[56] References Cited

U.S. PATENT DOCUMENTS

| | | | |
|---|---|---|---|
| 2,212,334 | 8/1940 | Wallerich | 264/330 |
| 2,857,915 | 10/1958 | Sheridan | 128/349 R |
| 2,940,126 | 6/1960 | Sheridan | 264/173 |
| 3,529,633 | 9/1970 | Vaillancourt | 138/118 |
| 3,749,134 | 7/1973 | Slingluff et al. | 138/118 |
| 3,847,157 | 11/1974 | Caillouette et al. | 138/118 |
| 3,907,955 | 9/1975 | Viennot | 264/173 |

Primary Examiner—Jeffery R. Thurlow
Attorney, Agent, or Firm—Andrus, Sceales, Starke & Sawall

[57] ABSTRACT

A catheter or other medical tube is formed by extruding of a suitable thermoplastic with an integral stripe portion simultaneously formed by extruding of the same or a compatible plastic material into the wall of the tube. The integral stripe portion has dispersed therein a powdered conducting metal or carbon and an X-ray opaque powdered salt such as a bismuth or bromide salt. The completely different functioning pigments may be incorporated in sufficient quantities to provide reliable dual functions without disrupting or otherwise adversely affecting the strength and characteristic of the tube for the purposes intended in the medical art. The stripe portion is preferably crowned to extend the exterior surface from the contiguous body of the tube and thus further provide additional carrier for the mixture of the two different pigments. The conductive pigment is also partially opaque and thus generally a mixture of 85% conductive pigment and 15% X-ray opaque pigment produces an exceptionally satisfactory construction. The integrated dual functioning stripe portion produces a single medical tube creating the advantages of the individual tubes heretofor provided in the art and thus usable in widely varying applications.

2 Claims, 2 Drawing Figures

RADIOGRAPHIC OPAQUE AND CONDUCTIVE STRIPED MEDICAL TUBES

This is a divisional application of application Ser. No. 634,075, filed Nov. 21, 1975, now U.S. Pat. No. 4,027,659.

BACKGROUND OF THE INVENTION

This invention relates to a radiographic opaque and conductive striped medical tube such as catheters, cannulae and other similar tubes which are introduced into the body cavity during medical procedures and in particular to such a tube which can be accurately located through radiographic observation and which eliminate possible hazardous electrostatic charge conditions.

Catheters and like cylindrical tubes for introduction to the body cavity are presently of rubber, vinyl and other thermoplastic materials. Extruded plastic materials are widely employed because of the economies of production which permit construction of disposable tubes. Such tubes have been constructed with an X-ray opaque stripe extending throughout the length of the tube. By directing a beam of X-rays through the body of the patient in the neighborhood of the inserted medical tube, the relative position of the catheter and the living tissue will appear on a fluoroscope or X-ray film. The stripe may include any suitable X-ray opaque pigment such as one of the bismuth salts. A highly satisfactory X-ray opaque medical tube is more fully disclosed in U.S. Pat. No. 3,749,134 wherein the tube is formed of suitable thermoplastic resin including a particular diol of a tetrabromophthalic anhydride to make the tube radiographic. In addition to location of the tube within the body cavity, care must often be taken such as under surgical procedures to avoid creation of electrostatic discharge conditions. Thus, plastic materials which are widely employed in surgical tubes are known to acquire electrostatic charges when brought in frictional contact with other bodies such as certain fabrics. This may create a highly hazardous condition in the presence of explosive gases such as will normally be encountered in surgical areas as a result of the use of various anesthetizing gases. Recommended safe-practice standards have been established requiring the use of electrically conductive elements within the tube to permit grounding and discharge of any electrostatic charge. It has even been suggested that the tube be formed with a suitable conductive strip formed by conductive particles dispersed throughout the strip portion of the tube. When using a pigment, consideration must be given to the strength characteristics of the tube and the like. Further, as the particles are completely of different characteristics and function in completely different manners, individual and separate stripes have been employed. The formation of a tube with the several different stripes and characteristics presents significant practical difficulties in the construction of a tube and generally the tubes have heretofor been constructed with either one or the other of the individual and separate functional portions.

SUMMARY OF PRESENT INVENTION

The present invention is particularly directed to medical tubes formed of a suitable flexible material and including an integral stripe portion containing a mixture of a highly conductive first material and a radiographic opaque second material intimately mixed and dispersed in the single stripe portion, whereby said single stripe portion is both operable for grounding of the tube and for radiographic observation of the tube's position. Generally, in accordance with the present invention, the medical tube is formed by extruding of a suitable plastic material or the like with the stripe portion simultaneously formed by extruding of the same or a compatible plastic material into the wall to form the separate but integral stripe portion which has dispersed therein the first and second materials and thereby form a single, fused longitudinally extending stripe portion within the tube. The two materials may be suitable pigments such as a powdered conducting metal or carbon, and an opaque powdered salt such as a bismuth or bromide salt. The inventor has found that the completely different functioning materials can be incorporated into the single stripe in sufficient quantities to provide reliable dual functions and with each material functioning without interfering with the functioning of the opposite material. The single stripe can be formed with a sufficient density in each of the integral materials without in fact disrupting or otherwise adversely affecting the strength and characteristic of the tube for the purposes intended in the medical art. The portion can be formed with a crown to extend the exterior surface from the contiguous body of the tube and thus further provide the desired carrier for the mixture of the two different pigments. Consequently, the integrated dual functioning stripe produces a single medical tube creating the advantages of the individual tubes heretofor provided in the art and thus usable in widely varying applications.

The present invention thus provides an improved universal medical tube and method of forming such a universal medical tube which can be carried out with conventional processing equipment so as to produce an inexpensive, reliable and high quality medical tube.

DESCRIPTION OF ILLUSTRATED EMBODIMENT

Figure 1:
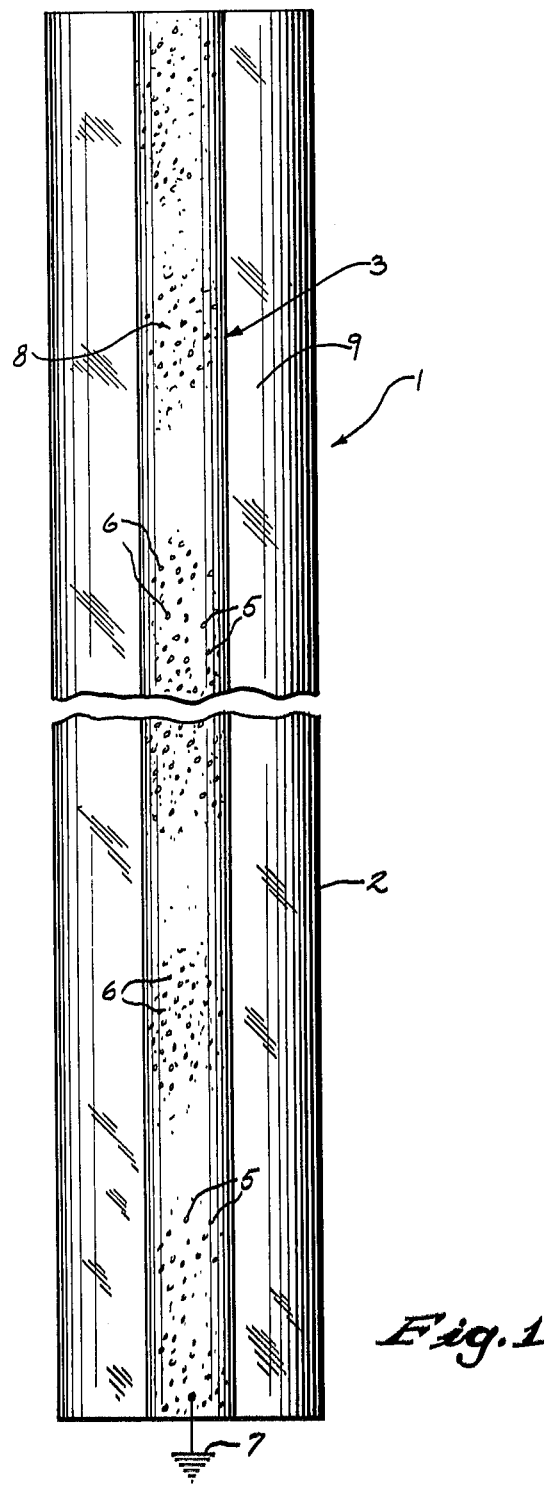
FIG. 1 is a plan view of a fragmentary portion of a surgical tube constructed in accordance with the teaching of the present invention.

Referring to the drawing, a medical tube 1 is illustrated including a tubular portion 2 within which an unique stripe portion 3, constructed in accordance with the present invention, is integrally formed and extending through the complete length thereof.

The tube body 2 and the stripe portion are formed of a suitable flexible plastic medium, such as a thermoplastic resin including polyethylene, vinyl polymers, and the like, as more fully discussed in the inventor's issued U.S. Pat. No. 3,749,134. The body portion 2 may be formed as a clear transparent portion for convenient visual inspection or may include a suitable dye to tint the tube while permitting inspection. The stripe portion 3 is preferably formed of the same plastic base material but may of course be any other suitable base material which is cohesively compatible with that of the tube 2 to form a single integral member.

In accordance with this invention, the base or carrier material 4 of the stripe portion 3 includes first and second particles or pigments 5 and 6. The first pigment 5 is a highly conductive material such as any suitable metal or other solid conductive particles which can be formed as very finely divided particles or powder. Generally, an electrically conductive carbon, which is readily available as a standard commercial product in powdered form is preferably employed because of its stable characteristic as well as good conductivity. The dispersing of the carbon pigment 5 throughout the tube portion 3 establishes an electrically conductive path. In use, the proximal end of the tube portion 3 is connected to a ground as shown diagrammatically at 7. Any suitable well known connector, not shown, can of course be employed. The grounded conductive path prevents the build up of an electrostatic charge, or retention of any previous charge, and the tube 1 may therefore be safely employed in surgical procedures and the like. The second pigment 6 is a suitable finely divided powder of a radio-opaque material such as the well known bismuth salts or, as disclosed in the inventor's U.S. Pat. No. 3,749,134, a bromide salt. These pigments are also readily available in commerce in finely divided powdered form and thus may be conveniently mixed with the conducting pigment 5.

In making of the unique radiographic opaque and conductive striped tube, conventional multiple orifice extrusion equipment can be employed. In such devices, the main visible body, portion 2 of the tube 1 is extruded through a major orifice of an extrusion die and simultaneously the longitudinally extending striped portion 3 is extruded through a minor orifice or orifices of the extrusion die. By the use of the same or compatible plastic materials in the body portion 2 and as the carrier 4 in the stripe portion 3, a single integral tube results with the dual functioning stripe formed therein.

Although the percentages of pigment loading are not critical, Applicant has generally found that it is advisable to maintain the total pigment loading of the tube stripe portion 3 below 70% (percent) by weight of the thermoplastic resin composition including the resin and plasticizers employed and preferably within the range of 15 to 40% by weight of such of the thermoplastic resin composition. Generally, the materials may be conveniently constructed with the conductive material 5 forming 85% of the total volume of added pigment and the radio-opaque material 6 constituting the other 15 percentage of the total added pigment. The ratio is not critical and may be varied to employ equal amounts of pigment. Generally, the conductive material particularly if a conductive carbon is employed predominates to insure good conductivity. Although not a conventional X-ray opaque material, the inventor has found that it does in fact produce some visual imaging and when combined with even relatively low proportions of X-ray opaque material produces a highly satisfactory dual functioning stripe portion.

Figure 2:
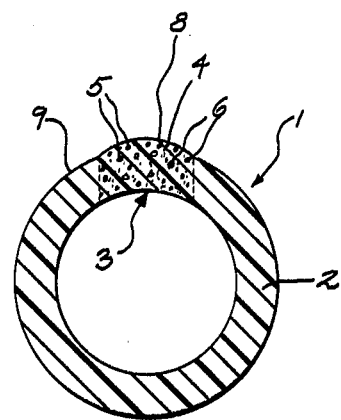
FIG. 2 is an enlarged section, transverse section taken along line 2—2 of FIG. 1.

The inventor has also found that the tube 1 is also advantageously formed with the exterior wall 8 of the stripe portion 3 protruding outwardly of the contiguous outer wall 9 of the body portion 2 of the tube 1, as most clearly shown in FIG. 2. This permits the somewhat greater volume of plastic carrier into which the two different pigments can be distributed. Thus the loading of the relatively thin body portion of the tube can be somewhat reduced, thereby insuring desirable strength characteristics and the like of the medical tube 1. The protruding portion is preferable formed as a crowned protruding configuration to define a smooth, continuous exterior surface.

The inventor has found that the incorporation of the two different materials in a common stripe portion can be readily provided without in any way adversely affecting the characteristic of the tube for the intended purposes and/or interfering with the complete reliable functioning of the X-ray transparent conductive material 5 and the non-conductive X-ray opaque material 6. The tubes may, of course, be formed with any desired cross-section and size and further treated for end connections and the like in accordance with the particular applications.

In use, the proximal end of the tube 1 is connected in any suitable well-known manner to a ground. Thus any electrostatic charge which tends to develop on the tube during use is automatically discharged to ground, maintaining a completely neutral tube condition, thereby essentially eliminating the hazardous conditions. Further, when exposed to an X-ray beam the location of the stripe appears distinctly to define the location, the precise location of the tube within the body cavity.

The present invention thus provides a simple and inexpensive construction of a medical tube which is both radiographically opaque and conductive such that it can be employed in both surgical and non-surgical procedures. The minimizing of the costs permits construction as a throw-away tube.

I claim:

1. The method of making a thermoplastic medicosurgical tubing which is radiographically opaque and conductive, comprising the steps of incorporating with a flexible, waterproof thermoplastic material which is non-conductive and which passes X-rays a mixture of a finely divided non-conductive radiographic opaque material and a finely divided radiographic transparent conductive material to form a thermoplastic composition, and forming a tubing of separate flexible, waterproof thermoplastic material which is non-conductive and which passes X-rays and of said thermoplastic composition with the thermoplastic composition located as an integral narrow strip extending longitudinally throughout the length of the tubing.

2. The method of claim 1 including the step of simultaneously extruding said thermoplastic composition with the separate thermoplastic material, said separate thermoplastic material being devoid of said mixture of said opaque and conductive material.

* * * * *